US006936699B2

(12) United States Patent
Peters

(10) Patent No.: US 6,936,699 B2
(45) Date of Patent: Aug. 30, 2005

(54) PURIFICATION OF PROTEIN INCLUSION BODIES BY CROSSFLOW MICROFILTRATION

(75) Inventor: Jörg Peters, Haan (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 10/275,797
(22) PCT Filed: Apr. 25, 2001
(86) PCT No.: PCT/EP01/04634
§ 371 (c)(1),
(2), (4) Date: Mar. 20, 2003
(87) PCT Pub. No.: WO01/85757
PCT Pub. Date: Nov. 15, 2001

(65) Prior Publication Data
US 2003/0171560 A1 Sep. 11, 2003

(30) Foreign Application Priority Data
May 8, 2000 (DE) .......................... 100 22 258

(51) Int. Cl.⁷ .............................. A23J 1/00; C12P 21/06
(52) U.S. Cl. ..................................... 530/412; 435/69.1
(58) Field of Search ............................... 435/69.1, 69.7; 530/412, 417; 428/304.4, 315.5; 210/198.2, 198.3; 241/1; 370/392; 436/132

(56) References Cited

U.S. PATENT DOCUMENTS

| 5,723,118 A | 3/1998 | Sebald ..................... 424/85.2 |
| 6,506,590 B1 | 1/2003 | Apeler et al. .......... 435/252.33 |

FOREIGN PATENT DOCUMENTS

| EP | 0613499 | 9/1994 |
| EP | 1022337 | 7/2000 |

OTHER PUBLICATIONS

Hehn et al., Nuclear magnetic resonance imaging of structural changes in skin under phonophoretically enhanced drug permeation, Jul. 1996, Pharmazeutische Industerie, vol. 586, No. 6, Abstarct.*

Laurie G W et al., Localization of Binding Sites for Laminin Heparan Sulfate Proteoglycan and Fibronectin on Basement Membrane Type IV Collagen, 1986 Journal of Molecular Biology, vol. 189, No. 1, Abstract.*

Marston, F., The Purification of Eukaryotic Polypeptides Synthesized in *Escherichia coli*, Biochem. J., 240: 1–12 (1986).

Bailey, et al., The Effect of Denaturants on the Crossflow Membrane Filtration of *Escherichia coli* Lysates Containing Inclusion Bodies, J. Membrane Sci., 131: 29–38 (1997).

Bailey, et al., Crossflow Microfiltration of Recombinant *Escherichia coli* Lysates after High Pressure Homogenization, Biotechnology & Bioengineering, 56(3): 304–310 (Nov., 1997).

Blum, et al., DnaK–Mediated Alterations in Human Growth Hormone Protein Inclusion Bodies, Biotechnology, 10: 301–304 (Mar., 1992).

(Continued)

Primary Examiner—Jon Weber
Assistant Examiner—Robert B. Mondesi

(57) ABSTRACT

The invention relates to a process for purifying and/or concentrating inclusion bodies (refractile bodies) in a highly concentrated particle-containing solution, in which process the inclusion body-containing suspension is directed tangentially past one or more semipermeable membranes, so that the inclusion bodies are retained behind the membranes and that substances having a relatively small molecular weight may pass through the membrane and/or be adsorbed to the membrane, and a purified and/or concentrated inclusion body suspension is obtained. In the same manner, cell wall particles are removed from a inclusion body suspension. The invention further relates to the use of a crossflow microfiltration unit for purifying and/or concentrating inclusion bodies in a suspension and for removing cell wall particles from a inclusion body preparation.

3 Claims, 14 Drawing Sheets

OTHER PUBLICATIONS

Bowden, et al., Structure and Morphology of Protein Inclusion Bodies in *Escherichia coli*, Biotechnology, 9: 725–730 (Aug., 1991).

Meyeroltmanns, R., Membran–Tangenitalflub–Filtrationssysteme, BioTec, 5: 918–921 (Oct., 1991).

Riesenberg, et al., High Cell Density Fermentation of Recombinant *Escherichia coli* Expressing Human Interferon Alpha 1, Applied Microbiology & Biotechnology, 34: 77–82 (1990).

Schoemaker, et al., Examination of Calf Prochymosin Accumulation in *Escherichia coli*: Disulphide Linkages Are a Structural Component of Prochymosin–containing Inclusion Bodies, EMBO J., 4(3): 775–780 (1985).

Schoner, et al., Isolation and Purification of Protein Granules From *Escherichia coli* Cells Overproducing Bovine Growth Hormone, Biotechnology, 151–154 (Feb., 1985).

Walker, S., Lyddiatt, A., "Aqueous Two–Phase Systems as an Alternative Process Route for the Fractionation of Small Inclusion Bodies", J. of Chromatography B: Biomedical Applications, 711: 185–194 (1998).

Bailey, S., Meagher, M., "Separation of Soluble Protein From Inclusion Bodies in *Escherichia coli* Lysate Using Crossflow Microfiltration", J. of Membrane Science, 166: 137–146 (2000).

Meagher, M., Barlett, R., Rai, V., Khan, F., "Extraction of rIL–2 Inclusion Bodies From *Escherichia coli* Using Cross–Flow Filtration", Biotechnology and Bioengineering, 43: 969–977 (1994).

Forman, S., DeBernardez, E., Feldberg, R., Swartz, R., "Crossflow Filtration For the Separation of Inclusion Bodies From Soluble Proteins in Recombinant *Escherichia coli* Cell Lysate", J. of Membrane Science, 48: 263–279 (1990).

Chem. Abstr. XP–002184947, Graham, E., Howell, J., "Fractionation of Proteins Using Ultrafiltration Membranes Retrieved From STN" (1998).

Sharma, S., Recovery of Soluble Human Renin From Inclusion Bodies Produced in Recombinant *Escherichia coli*, J. Biotechnology, 4: 119–124 (1986).

Taylor, et al., Size and Density of Protein Inclusion Bodies, Biotechnology, 4: 553–557 (Jun. 1986).

\* cited by examiner biomass loads:
(kg of wet cell mass equivalent/m²)

biomass load:
(kg of wet cell mass equivalent/m²)

biomass load:
(kg of wet cell mass equivalent/m²)

A

B

PURIFICATION OF PROTEIN INCLUSION BODIES BY CROSSFLOW MICROFILTRATION

The invention relates to a process for purifying and/or concentrating inclusion bodies (refractile bodies) in a highly concentrated particle-containing solution, in which process the inclusion body-containing suspension is directed tangentially past one or more semipermeable membranes, so that the inclusion bodies are retained behind the membranes and that substances having a relatively small molecular weight may pass through the membrane and/or be adsorbed to the membrane, and a purified and/or concentrated inclusion body suspension is obtained. In the same manner, cell wall particles are removed from a inclusion body suspension. The invention further relates to the use of a crossflow microfiltration unit for purifying and/or concentrating inclusion bodies in a suspension and for removing cell wall particles from a inclusion body preparation.

DESCRIPTION

The present invention relates to a process for purifying and/or concentrating inclusion bodies in a highly concentrated, particle-containing solution, to a process for removing cell wall particles from a inclusion body suspension and also to the use of a crossflow microfiltration unit for purifying and/or concentrating inclusion bodies in a suspension and for removing cell wall particles from a inclusion body preparation.

DEFINITION OF TERMS

Inclusion bodies (refractile bodies) are often formed in the case of high expression of heterologous or homologous proteins in *Escherichia coli* and consist of highly aggregated proteins, nucleic acids, enzymes of protein biosynthesis and ribosomes. Inclusion bodies are electron-dense amorphous particles which have a discrete border to the cytoplasm but are not surrounded by a membrane (Schoemaker J M et al. (1985): EMBO J 4:775–780). During the preparation of inclusion bodies, various types of interactions may lead to secondary adsorption of other contaminations such as, for example, endotoxins, cell wall debris and lipids (Marston FAO (1986): Biochem. J. 240: 1–12).

Biomass here denotes the sum of all high-molecular-weight and low-molecular-weight components occurring in a cell lysate. In particular the proportion of cell wall debris (cell wall particles) and of inclusion bodies, but also components such as nucleic acids, endotoxins, soluble protein and low-molecular weight components determine the physicochemical properties of the material to be filtered. Information on biomass concentrations is always based on the concentration of wet cell weight before cell lysis. This is called biomass equivalent.

The transmembrane pressure (TMP) is defined as:

$$TMP = (\text{inlet pressure} + \text{outlet pressure})/2 - \text{permeate pressure} \ \{bar\}$$

The inlet pressure is the pressure at the retentate inlet (inlet opening of the cassette).

The outlet pressure is the pressure at the retentate outlet (outlet opening of the cassette). The permeate pressure is the pressure at the permeate (filtrate) outlet.

Transmission here means the removal of soluble components via the membrane into the permeate. For this purpose, samples are drawn from the permeate and the retentate at various times (x) during diafiltration and centrifuged (14 000×g, 15 min), and the soluble supernatant, after suitable dilution, is photometrically measured at 280 nm (optical density at 280 nm). The $OD_{280}$ data of the permeate at each time x ($OD_{280}(\text{permeate}(x))$) are then related to the $OD_{280}$ data of the retentate at each time x ($OD_{280}(\text{retentate}(x))$) according to the following formula:

$$\text{transmission} = OD_{280}(\text{permeate}(x))/OD_{280}(\text{retentate}(x)) \times 100$$

The transmission typically changes during the course of a diafiltration. Initially, the membrane is still free of adsorbed components and has no covering layer. Therefore, transmission at the start of the filtration is 100% by definition. However, it typically declines during filtraiton, since more and more covering layer is formed which prevents the transport of soluble components via the membrane into the permeate. Thus, the transmission can globally be stated only as an average (average transmission).

Removal here means the removal of soluble components from the retentate. In this connection, samples are drawn from the retentate at various times (x) during the diafiltration and centrifuged (14 000×g, 15 min) and the soluble supernatant, after suitable dilution, is measured photometrically at 280 nm (optical density at 280 nm). The $OD_{280}$ data ($OD_{280}(\text{retentate}(x))$) are then related to the $OD_{280}$ value of the soluble supernatant, which value was originally present in the retentate ($OD_{280}(\text{retentate}(0))$):

$$\text{removal} = 100 - (OD_{280}(\text{retentate}(x))/OD_{280}(\text{retentate}(O)) \times 100)$$

The removal typically approaches a maximum up to the end of the diafiltration. The data thus represent the maximum removal reached of soluble components.

PRIOR ART

In protein chemistry, inclusion body purification processes are customary methods. In laboratory processes known from the prior art, the biological material obtained (*E. coli* bacteria cells) is, for example, centrifuged after its lysis (commonly using enzymatic lysis by lysozyme, ultrasound treatment or high pressure homogenization), and the sediment obtained which contains the inclusion bodies and contaminations such as non-lysed cells, cell envelopes and cell wall fragments is washed with buffer with the aid of sedimentation or, alternatively, by crossflow microfiltration. Although the process of sedimentation is generally utilized for purifying inclusion bodies after their release from the cells (e.g. Schoner R G et al. (1985): Biotechnology 3: 151–154; Sharma S K et al. (1986): J. Biotechnol. 4: 119–124), this process may cause difficulties on a larger scale (Forman S M et al. (1990): J. Membr. Sci. 48: 263–279). The inclusion bodies may be washed with the aid of crossflow microfiltration up to the purity desired (Meagher M M et al. (1994): Biotechnol. Bioeng. 43: 969–977; Forman S M et al. (1990): J. Membr. Sci. 48: 263–279).

The average particle size of inclusion bodies is dependent on the particular target protein expressed, the host strain, the expression system and the culture medium used and may be in the range from 0.07 μm for human growth hormone (Blum P et al. (1992): Bio/Technology 10: 301–304) to 1.5 μm for β-lactamase (Bowden G A et al. (1991): Bio/Technology 9: 725–730). Further examples from the literature are prochymosin inclusion bodies with particle diameters of 1.26 μm (±1.2 μm) and interferon with 0.81 μm (±0.4 μm) (Taylor G et al. (1986): Bio/Technology 4: 553–557). However, cell wall debris has, depending on the process of lysis, particle sizes between 0.05 μm and 1 μm (Bailey S M and Meagher M M (1997): Biotechnol. Bioeng. 56(3): 304–310). Moreover, the extent of lysis also affects the particle size distribution in the crude homogenate. Thus, many crude homogenates have overlapping particle size distributions between inclusion bodies, cell wall debris and non-lysed cells.

Forman et al. state a logarithmic relation between the permeate flux and the increasing biomass concentration in the product solution to be filtered. That is to say that the permeate flux drops off drastically when the initial biomass concentration in the product solution to be filtered increases. Forman et al. state maximum permeate fluxes of 14 l/h m$^2$ at 25 g/l (2.5%) biomass equivalent, 12 l/h m$^2$ at 50 g/l (5%) biomass equivalent and <8 l/h m$^2$ at 100 g/l (10%) biomass equivalent for a Durapore® membrane (Millipore) having an exclusion limit of 0.45 $\mu$m. The biomass load of the membrane in these experiments was at about 1.4 kg of wet cell mass equivalent/m$^2$. At a given biomass concentration in the product solution, increasing the permeate flux to above a particular limit results in a dramatic increase of TMP and thus in the clogging of the membrane pores (fouling). Conversely, the permeate flux at a given TMP drops off over the filtration period.

Other research groups (Bailey S M & Meagher M M (1997): J. Membr. Sci. 131: 29–38) state that, in the case of polysulphone hollow fibre modules or polyvinylidene fluoride (PVDF) cassette modules, permeate flux and transmission decline over time even at biomass loads of 4–6% (40–60 g/l), and this is exacerbated by the addition of chaotropic agents such as guanidine hydrochloride.

Meagher and coworkers (Meagher M M et al. (1994): Biotechnol. Bioeng. 43: 969–977) reported similar results for the purification of IL-2 inclusion bodies on a Durapore ® membrane (polyether sulphone, 0.1 $\mu$m). At a biomass concentration of 7% (70 g/l) wet cell mass equivalent in the retentate, both protein transmission and permeate flux (20–10 l/h m$^2$) decrease significantly over the filtration period, and this was attributed to the formation and compression of a membrane covering layer. The adsorption of protein on the membrane depends on the physicochemical properties of both the protein solution and the membrane itself.

Thus there are no processes known from the prior art which make it possible to filter inclusion body solutions at very high biomass concentrations and constant operating parameters (pressure, permeate flux, retentate flow). No direct information on the reproducibility of the characteristic filtration parameters over many filtration cycles can be found in the literature. This has so far prevented the transfer of crossflow microfiltration processes for fine purification of inclusion body-containing suspensions to the industrial scale.

SUBJECT OF THE INVENTION

It was therefore an object of the present invention to provide a purification and concentration process based on crossflow microfiltration, which process makes it possible in a simple manner to purify inclusion bodies in industrially relevant amounts with constant operating parameters during one and over many filtration cycles. Another object of the present invention was to lower the concentration of cell wall particles and other low-molecular-weight components such that subsequent processing steps, in particular refolding of the denatured target protein and chromatographic final purification, succeeds reproducibly with industrially relevant yields.

In a first aspect, the present invention relates to a process for purifying and/or concentrating inclusion bodies in a solution, which is characterized in that the protein inclusion body-containing solution is directed tangentially past one or more semipermeable membranes so that the membranes retain the inclusion bodies and that substances or components having a relatively small molecular weight or particle diameter can pass through, thus obtaining a purified and/or concentrated inclusion body solution.

In another aspect, the present invention relates to a process for removing cell wall particles from a inclusion body preparation, which is characterized in that the inclusion body-containing preparation is directed tangentially past one or more semipermeable membranes, so that the inclusion bodies are retained by the membranes and that substances or components having a relatively small molecular weight or particle diameter can pass through and/or are adsorbed to the membranes, leading to an essentially particle-depleted inclusion body solution.

The present invention relates to a process for purifying and/or concentrating inclusion bodies in a solution, which is characterized in that the inclusion body-containing solution is directed tangentially past one or more semipermeable membranes so that the membranes retain the inclusion bodies and that substances or components having a relatively small molecular weight or particle diameter can pass through, thus obtaining a purified and/or concentrated inclusion body solution, and on the semipermeable membrane a wide-meshed matrix is located which is constructed of intersecting longitudinal and transverse filaments such that the adjacent longitudinal and transverse filaments are, in each case, at a distance from one another which is 5 to 15 times greater than their thickness which is in the range from 150 to 600 $\mu$m.

It has been found now that it is possible to purify and concentrate inclusion bodies by the process of the present invention using a crossflow microfiltration unit. A surprising and novel fact in this connection is in particular that the inclusion bodies can be filtered at a stable operating point even with a high load of soluble and particulate components (biomass) in the starting preparation, without the membrane being blocked and/or the filtration performance being reduced by the formation of a covering layer. Until now, the achievable biomass concentrations in the retentate have been low. At high biomass concentrations, however, blockage of the retentate channel causes an increasing change in the operating point during the filtration cycle or over several operating cycles, causing the retentate flow and also the permeate flux to decrease steadily. After a plurality of cycles, the permeate fluxes which can be achieved no longer enables economically attractive operation. Cleaning of the membranes blocked in this way proves to be complicated and usually incomplete.

At low biomass loads of the membrane on the other hand, which cause relatively few blockage problems, an extremely large filtration area is needed, in particular on an industrially relevant scale, and this has a negative effect on the economy of the crossflow microfiltration step.

Therefore, crossflow microfiltration has not hitherto been used for purifying and concentrating inclusion body preparations on an industrially relevant scale and at high biomass concentrations.

However, the modified cellulose hydrate membrane cassette used here suprisingly facilitates filtration of inclusion bodies at a stable operating point even at a high load of soluble and particulate components (biomass) in the starting preparation, without the membrane being blocked and/or filtration performance being reduced by the formation of a covering layer. The stable operating point is maintained surprisingly also over many filtration cycles The process of the present invention purifies and/or concentrates inclusion bodies at high biomass concentrations between 50 g/l and 2 500 g/l, preferably between 500 g/l and 1 500 g/l. The choice of the cut-off of the membrane depends on the average particle diameter and particle size distribution of the inclusion bodies. For the modified hydrophilic cellulose hydrate membrane used according to the invention, the cut-off may be between 0.1 and 0.65 μm, preferably at 0.45 μm.

Any size of volume can be processed, and preferably a solution having a volume of from 1 to 100 000 l and particularly preferably of from 1–2 000 l is processed. The solution containing the inclusion bodies is directed past the membrane(s) under suitable pressure conditions, the overflow pressure preferably being greater than the transmembrane pressure (TMP). The operating pressure is preferably a TMP of from 0.05 to 3 bar, particularly preferably a TMP of from 0.1 to 0.5 bar, and most preferably a TMP of from 0.2 to 0.4 bar, the overflow pressure being greater than the transmembrane pressure. The retentate flow may vary over a wide range and should be chosen such that a turbulent flow is achieved (Reynolds number >30; Meyeroltmanns F (1991): BioTec 5: 918–921). To decrease the minimum retentate flow at which a turbulent flow is achieved, screens are built into the membrane modules employed according to the invention. The shape and geometric arrangement of the said screens is described in a separate patent application with the title "Crossflow filter cassettes in the form of improved wide-gap modules", filed on the same day.

For the biomass load, a distinction must be made between the biomass concentration in the retentate (in g/l) and the area-specific biomass load (in kg/m²). A retentate biomass concentration which is too high may lead to the blockage of retentate channels, whereas an area-specific biomass load which is too high leads to the formation of a covering layer on the membrane (fouling).

The retentate biomass concentration of the modified cellulose hydrate modules employed here may be up to 1 500 g/l, while the area-specific biomass load may be increased to 30 kg/m².

The process may also be carried out at varying temperatures. Preference is given to a temperature range from 4° C. to 40° C.

In a further aspect of the invention, the inclusion body preparation prepared according to the invention shows a significantly lower endotoxin contamination compared to the starting material.

EXAMPLES

In the experiments described, screen channel modules which had been modified in various ways and which are equipped with a Hydrosart® membrane made of modified cellulose hydrate (Sartorius A G, Germany) were used. The modules differ substantially in the geometric form of the matrix. The Hydrosart® membrane is commercially available with exclusion limits of 0.1, 0.2, 0.45 and 0.65 μm.

TABLE 1

Characteristic data of the modified Hydrosart ® modules employed

| Module Lot No. (Sartorius AG) | Description of module type | Module type Filter area | Geometric information on the retentate channel | Information on the screen |
|---|---|---|---|---|
| 98025101 | #1 | Slice module 0.1 m² | Membrane/matrix distance: 125 μm<br>Matrix thickness: 470 μm<br>Filament thickness: 210 μm<br>Filament distance: 250 μm<br>Angle to flow direction: 30° & 60° | Mesh |
| 98055101 | #2 | Slice module 0.05 m² | Membrane/matrix distance: 80 μm<br>Matrix thickness: 1 030 μm<br>Filament thickness: 500–650 μm<br>Filament distance: 1 500 μm<br>Angle to flow direction: 45° | Extruded, planar net |
| 99015111 | #3 | Slice module 0.1 m² | Membrane/matrix distance: 80 μm<br>Matrix thickness: 760 μm<br>Filament thickness: 340–450 μm<br>Filament distance: 2 400 μm<br>Angle to flow direction: 45° | Extruded, planar net |
| 99015012 | #3 | Sartocon 2/3-module 0.46 μm² | Membrane/matrix distance: 80 μm<br>Matrix thickness: 760 μm<br>Filament thickness: 340–450 μm<br>Filament distance: 2 400 μm<br>Angle to flow direction: 45° | Extruded, planar net |

Table 1 Characteristic data of the modified Hydrosart® modules employed

1. Preparation of a Starting Solution

*E. Coli* W3110 cell mass containing a target protein in the form of inclusion bodies (for example interleukin-4 R121D Y124D) was prepared by fermentation according to the prior art (Riesenberg et al., 1990: Appl. Microbiol. Biotechnol. 34: 77–82). After enzymatic lysis (lysozyme: 1 mg/g dry cell mass), the cells were disrupted at a wet biomass concentration of 30–40% with the aid of a standard homogenizer (Bran & Lübbe, Germany). The buffer used was 100 mM Tris-HCl (pH 8) with 5 mM ethylenediaminetetraacetic acid (EDTA). The mechanical cell lysis was accomplished in three homogenization cycles at 500 bar. The degree of lysis was approx. 80–90%, as determined by image analysis. The crude homogenate obtained was subsequently concentrated with the aid of a separator (Westfalia, Germany), the total dry matter being collected in the sludge. The flowable sediment was subsequently cryopelleted in liquid nitrogen and stored at −70° C. until further use for the filtration experiments.

With the aid of the said process, three independent batches of crude homogenate were prepared and stored as cryopellets at −70° C. until further use.

2. Measurement of Endotoxin Removal After Crossflow Microfiltration

Samples of the inclusion body-containing solutions (retentate before diafiltration, retentate after diafiltration) and the total permeate are analysed with the aid of the limulus amoebocyte lysate process according to the European Pharmacopoeia (Pharm. Eur.). Testing for endotoxins was carried out according to the "solid gel" process in which the addition of an endotoxin-containing solution to a limulus amoebocyte lysate solution (LAL solution) causes the mixture to form a gel. The gel formation is based on a coagulation cascade proceeding in several steps.

3. Crossflow Microfiltration with Standard Hydrosart® Module

Unit Structure:

A crossflow microfiltration unit typically consists of the components depicted in FIG. 10.

Determination of Water Values:

To determine water values, the unit is run with deionized water, and the following pressures are set with the aid of the flow restrictor valves (4 & 5):

| R(in): | 2 bar | TMP: | 1 bar |
|---|---|---|---|
| R(out): | 1 bar | | |
| P: | 0.5 bar | | |

The flows are determined in each case at the retentate outlet and the permeate outlet. The measurement serves to determine the state of the cassettes prior to the first use and prior to or following each product cycle.

The entire unit is then adequately rinsed with wash buffer (0.05 M tris-HCl pH 7, 5 mM ethylenediaminetetraacetate $Na_4$, 0.1% Zwittergent 3–14). The flow restrictor valve for the permeate outlet (5) is closed and the pump is stopped. The retentate reservoir is emptied and subsequently charged with inclusion body suspension.

Rinsing in the Crude Homogenate and Starting the Unit

A portion of the cryo-pelleted crude homogenate, equivalent to 300 g of the original wet cell mass for example, is thawed and introduced to a separate retentate reservoir. Wash buffer (0.05 M tris-HCl pH 7, 5 mM ethylenediaminetetraacetate-$Na_4$, 0.1% Zwittergent 3–14 (Fluka)) is added to the suspension up to the total retentate volume stated minus the dead volume, and the reservoir is connected to the pump inlet. The dead volume of the unit is 0.55 l. The pump is started with closed permeate flow restrictor valve (5) and the retentate is pumped in circulation for approx. 5 minutes. The following pressures are set by adjusting the pump output (R(in)) or with the aid of the flow restrictor valve:

| R(in): | 1 bar | TMP: | 0.35 bar |
|---|---|---|---|
| R(out): | 0.5 bar | | |
| P: | 0.4 bar | | |

In this connection, the permeate valve is opened particularly carefully in order to prevent compressing a covering layer which may be present on the membrane. From the stated settings, a transmembrane pressure (TMP) of 0.35 bar is calculated, which pressure has been found to be optimal in operating point determinations carried out previously.

Diafiltration

During the diafiltration which then follows, the retentate volume is exchanged up to five times. The retentate volume is maintained at a constant level by continuous addition of wash buffer.

After in each case 0.5 l of permeate volume, the pressure settings are checked and documented (constant TMP of 0.35 bar) and samples are drawn from the retentate and permeate. In addition, the retentate flow and the permeate flow are determined.

Concentration

At the end of the diafiltration, the retentate may optionally be concentrated to about 50% of the original volume by interrupting the wash buffer feed.

Removing the Retentate

To remove the retentate, the permeate flow restrictor valve (5) is slowly closed and the retentate is pumped in circulation. Then 0.5–1 l wash buffer (=1 to 2× dead volume) is introduced into the unit and the retentate is emptied completely into the retentate reservoir.

Cleaning the Unit

The unit is first rinsed with 2l of 0.9% NaCl solution, with the permeate flow restrictor valve (5) remaining closed. The pump output is set such that the pressure at the retentate inlet (R(in)) is 3 bar. The flow restrictor valve at R(out) (7b) is opened completely. Then a further 2 l of 0.9% NaCl solution are pumped in the retentate circulation for approx. 10 minutes.

The unit is subsequently rinsed with 2.5 l of 2% strength citric acid solution. The pressure settings remain the same. The first 0.5 l is discharged from the unit, and subsequently the solution is run in the retentate circulation for approx. 10 minutes.

The citric acid cleaning solution is rinsed out with approx. 20 l of deionized water. Then 2.5 l of 1% strength Ultrasil-62 solution (Henkel A G, Germany), heated to approx. 40° C., are rinsed in. The pressure settings remain the same. The first 0.5 l is discharged from the unit and subsequently the solution is run in the retentate circulation for approx. 10 minutes. The Ultrasil cleaning solution is again rinsed out with approx. 20 l of deionized water.

Finally, the unit is cleaned with 2.5 l of a 1 N NaOH solution which is heated to 40° C. The pressure settings remain the same. The first 0.5 l is discharged from the unit and subsequently the solution is run in the retentate circulation for approx. 10 minutes. Then the flow restrictor valve at the permeate outlet (5) is completely opened. This is followed by removing the sodium hydroxide solution from the unit by rinsing with approx. 20 l of deionized water.

At the end, the water values are determined once again (see above).

Storing the Cassettes

For a short period (up to 7 days), the complete unit including the built-in cassettes can be stored in deionized water. For longer periods of inactivity (>7 days), the complete unit including the built-in cassettes is stored in 20% aqueous ethanol.

In-Process Monitoring

The samples are centrifuged (14 000×g, 15 minutes) and appropriately diluted with wash buffer. Subsequently, OD at 280 mn is measured against a reference cuvette (wash buffer) in a commercial spectrophotometer.

Using the experimental protocol described and starting from a uniform portion of the crude homogenate (see Example 1), a plurality of filtration cycles was run.

Results

The results of the first diafiltration cycle (novel Hydrosart® Slice membrane (0.1 m², 0.45 μm)) of *E. coli* crude homogenate (portion #1) with inclusion bodies of interleukin-4 R121D Y124D are summarized in FIG. 1. The removal of soluble components from the retentate increases with filtration time and finishes after 3.3 volume exchanges on a plateau of 55%. Starting from 100%, which corresponds to a completely free membrane, the transmission steadily decreases down to a final value of 9% after 3.3 volume exchanges. The retentate flow is substantially constant at 46–48 l/h. The permeate flux steadily decreases from 82 l/h $m^2$ to 27 l/h $m^2$ after 3.3 volume exchanges.

Prior to the product run, the water values of the novel membrane module were determined as 37.2 l/h (retentate flow) and 1 968 l/h $m^2$ (permeate flux). After the product run and cleaning of the module (see above), just 22.8 l/h (retentate flow) and 1 800 l/h $m^2$ (permeate flux) were measured.

In the immediately following product cycle, exactly the same starting conditions were produced and the same starting product was used. The initial water values were at 22.8 l/h (retentate flow) and 1 848 l/h $m^2$ (permeate flux). After rinsing in the crude homogenate, the retentate flow fell to 2.5 l/h and the permeate flux to 2 l/h $m^2$ after only 1.5 l permeate volumes. As a result, the product run was aborted and the unit was reset to the initial state according to the above protocol. The water values after cleaning the unit were 19.4 l/h (retentate flow) and 1 704 l/h $m^2$.

In the immediately following product cycle, exactly the same starting conditions were again produced (see above) and the same starting product was employed. The water values prior to the product run were at 19.6 l/h (retentate flow) and 1 680 l/h $m^2$ (permeate flux). In this cycle, however, it was impossible to rinse the crude homogenate suspension into the unit. The retentate channel was immediately blocked. As a result, the product run was aborted and the unit was reset to the initial state according to the above protocol. It was no longer possible to clean the cassette according to the standard cleaning protocol described above.

Conclusion

On the basis of the water values stated for retentate flow and permeate flux and also on the basis of the mentioned retentate flows and permeate fluxes for the product run, it is evident that particle deposition blocked the retentate channel at 230 g of wet cell mass equivalent/l. The membrane itself was also significantly blocked by the formation of a covering layer at a biomass load of the membrane of 300 g of wet cell mass/$m^2$ over only three cycles.

4. Crossflow Microfiltration with Modified Hydrosart® Modules

The experimental arrangement, procedure and cleaning protocols were chosen as in Example 1. Preparation of the starting material (see Example 1) and also the biomass load of the membrane (3 kg of wet cell mass equivalent/$m^2$) and the biomass concentration (230 g of wet cell mass equivalent/l) were identical to the conditions mentioned in Example 2.

Three modified Hydrosart® modules having different types of screens and channel geometries were tested (see general part of the examples section). The membrane itself was not varied (Hydrosart® with exclusion limit of 0.45 μm).

4.1 Results with the Type#1 Module

FIG. 2 illustrates by way of example the first diafiltration cycle (novel Hydrosart® Slice module type#1, $0.1\ m^2$, 0.45 μm) of *E. coli* crude homogenate (portion #1) with inclusion bodies of interleukin-4 R121D Y124D. The removal of soluble components from the retentate increases with filtration time and finishes after 3.3 volume exchanges on a plateau of 61%. Starting from 100%, which corresponds to a completely free membrane, the transmission steadily decreases down to a final value of 9% after 3.3 volume exchanges. The retentate flow is substantially constant at 81–86 l/h. The permeate flux steadily decreases from 82 l/h $m^2$ to 21 l/h $m^2$ after 3.3 volume exchanges.

Prior to the product run, the water values of the newly purchased modified membrane module were determined as 52.8 l/h (retentate flow) and 2 136 l/h $m^2$ (permeate flux). After the product run and cleaning of the module (see above), just 46.8 l/h (retentate flow) and 1 968 l/h $m^2$ (permeate flux) were measured.

The retentate flows and the permeate fluxes in the product run of the following 7 product runs are summarized in FIG. 3*a*. The retentate flow in the product run decreases from 86 l/h in the first cycle to 19 l/h in the eighth cycle. The greatest fall in the retentate flow in the product run was observed between the first and the second cycle. The average permeate flux varies between 15 and 35 l/h $m^2$.

The removal of soluble components from the retentate is between 60% and 80% in all product runs. The average transmission is between 40% and 80%.

The results from cleaning the Hydrosart® type#1 module, i.e. the water values prior to and after product run for retentate flow and permeate flux, are depicted in FIG. 3*b*. The steady decrease of the retentate water value over the cycles and its virtual collapse in the 5th cycle are clearly visible. As for the standard Hydrosart® cassette, this indicates a blocking problem at the retentate inlet.

The water values for the permeate flux drop off within 8 cycles from 2 136 l/h $m^2$ to 1 344 l/h $m^2$, i.e. by 37%. The efficiency of the individual cleaning step is between 87% (worst step efficiency) and 100% (best step efficiency).

Conclusion

The modified Hydrosart® cassette type#1 already shows distinctly improved performance data and it was possible to use it over eight product runs, although the standard Hydrosart® cassette was irreversibly blocked under the same conditions after only three product runs.

Nevertheless, the problem of blocking of the retentate channel over the cycles still appears for the channel geometry and screen structure used in type#1, Due to the continuous changes within a product cycle and over a plurality of cycles, it is also impossible to maintain a stable operating point with the type#1 module.

4.2 Results with the Type#2 Module

FIG. 4 illustrates by way of example the first diafiltration cycle (novel Hydrosart® Slice module type#2, $0.05\ m^2$, 0.45 μm) of *E. coli* crude homogenate (portion #1) with inclusion bodies of interleukin-4 R121D Y124D. The removal of soluble components from the retentate increases with filtration time and finishes after 3.8 volume exchanges on a plateau of 75%. Starting from 100%, which corresponds to a completely free membrane, the transmission steadily decreases down to a final value of 25% after 3.8 volume exchanges. The average transmission is at 53%. The retentate flow is substantially constant at 190 l/h. Starting from an initial value of 156 l/h $m^2$, the permeate flux decreases steadily and finishes at a value of 38 l/h $m^2$.

Prior to the product run, the water values of the newly purchased modified membrane module were determined as 648 l/h (retentate flow) and 3 744 l/h $m^2$ (permeate flux). After the product run and cleaning of the module (see above), 708 l/h (retentate flow) and 3 720 l/h $m^2$ (permeate flux) were measured.

The retentate flows and the permeate fluxes in the product run of the following 6 product runs are summarized in FIG. 5a. The retentate flow in the product run is substantially constant and varies around 185 l/h. No collapse in the retentate flow in the product run is observed. The average permeate flux varies around 50 l/h m$^2$.

The removal of soluble components from the retentate is between 60% and 80% in all product runs. The average transmission is between 45% and 75%.

The results from cleaning the Hydrosart® type#2 module, i.e. the water values prior to and after product run for retentate flow and permeate flux, are depicted in FIG. 5b. The water values for the retentate flow decrease slightly and are between 650–700 l/h in the 1st cycle and 580 l/h in the last cycle. This indicates that the blocking problem at the retentate inlet is distinctly reduced compared to the standard Hydrosart® cassette and to the modified Hydrosart ® type#1 module.

The water values for the permeate flux drop off within 7 cycles only slightly from 3 744 l/h m$^2$ to 3 408 l/h m$^2$, i.e. by only 9%. The efficiency of the individual cleaning step is between 92% (worst step efficiency) and 105% (best step efficiency).

Conclusion

The modified Hydrosart® cassette type#2 already shows distinctly improved performance data compared with the standard Hydrosart® module and compared with the Hydrosart® type#1 module and it was possible to use it over seven product runs, although the standard Hydrosart® cassette was irreversibly blocked under the same conditions after only three product runs.

For the channel geometries and screen structures used in the Hydrosart® type#2 module, the problem of blocking of the retentate channel over the cycles is significantly reduced. Due to the constant conditions within one product cycle and over a plurality of cycles, it is possible to maintain a stable operating point with the Hydrosart® type#2 module even at a biomass load of 3 kg of wet cell mass equivalent/m$^2$ (230 g of wet cell mass equivalent/l).

4.3 Results with the Type#3 Module

FIG. 6 illustrates by way of example the first diafiltration cycle (novel Hydrosart®-Slice module type#3, 0.1 m$^2$, 0.45 μm) of E. coli crude homogenate (portion #2) with inclusion bodies of interleukin-4 R121D Y124D. In these experiments, the retentate volume was lowered to 1.3 l (0.55 l dead volume). The removal of soluble components from the retentate increases with filtration time and finishes after only 3.8 volume exchanges on a plateau of 77%. Starting from 100%, which corresponds to a completely free membrane, the transmission steadily decreases down to a final value of 13% after 3.8 volume exchanges. The retentate flow is substantially constant at 129–132 l/h. The permeate flux is practically constant at an average of 31.7 l/h m$^2$ (±2.95).

Prior to the product run, the water values of the newly purchased modified membrane module were determined as 105.6 l/h (retentate flow) and 1 320 l/h m$^2$ (permeate flux). After the product run and cleaning of the module (see above), 110.4 l/h (retentate flow) and 1 344 l/h m$^2$ (permeate flux) were measured.

A parallel experiment was carried out with a Durapore® V-Screen cassette (exclusion limit 0.45 μm, filter area 0.1 m$^2$, hydrophilized polyvinylidene fluoride (PVDF), open channel module) under the same conditions. The same experimental arrangement as described in Example 2 was chosen. However the cassette holder was exchanged for a corresponding holder for the Durapore® membrane. The biomass load (crude homogenate portion #2) in this experiment was likewise 3 kg of wet cell mass equivalent/m$^2$ or 230 g of wet cell mass equivalent/l. The retentate volume was 1.3 l and 3.8 volume exchanges were carried out (5 l permeate volume). The retentate flow was 90 l/h. The initial TMP was fixed at 0.3 bar. In this experiment however, TMP was not held constant, as in all other experiments, but the permeate flux was fixed to a value of 38 l/h m$^2$. An increase in the TMP shows to the same extent the blocking of membrane pores as it shows in the other experiments the decrease in the permeate flux.

After 3.8 volume exchanges, a removal of 70% was obtained. Transmission decreased from initially 100% to 10%. The TMP increased during the filtration from 0.3 bar to 0.65 bar. The retentate flow was not followed in this experiment.

Conclusion

The Hydrosart® type#3 module shows better performance data compared to the Durapore® V-Screen module under the same conditions. The Hydrosart® type#3 module removes approx. 80% of the soluble protein content from the retentate, while the Durapore® V-Screen module achieves about 70% removal. The changes in transmission are in both cases comparable. In particular however, the permeate flux (and the TMP) are nearly constant with the Hydrosart® type#3 module, while the TMP increases distinctly (and the permeate flux decreases) in the case of the Durapore® V-Screen module, as was also observed for the other module types tested.

4.3.1 Increasing Stepwise the Biomass Load of the Membrane

Owing to the fact that, when using the Hydrosart® type#3 module, both the retentate flow and the permeate flux stay practically constant over the filtration period, the biomass load of the membrane and the biomass concentration in the retentate were increased stepwise up to a factor of 5 in the following series of experiments. A second portion of the crude homogenate (#2) was used therein.

The retentate flows and permeate fluxes in the product run of the following 4 product runs with increasing biomass loads of the membrane are summarized in FIG. 7a. The retentate flow in the product run decreases from 130 l/h in the first cycle with 3 kg of wet cell mass equivalent/m$^2$ to 100 l/h in the fourth cycle with 15 kg of wet cell mass equivalent/m$^2$. Thus, for a 500% increase in the biomass load, the retentate flow decreases only by 23%. The average permeate flux decreases from 30 l/h m$^2$ at 3 kg of wet cell mass equivalent/m$^2$ in the first cycle to 10 l/h m$^2$ at 15 kg of wet cell mass equivalent/m$^2$ in the fourth cycle. The permeate flux is thus reduced by 50% for an increase of 500% in the biomass load.

The removal of soluble components from the retentate is 75% at 3 kg of wet cell mass equivalent/m$^2$ and varies around 60% when increasing the biomass load to 5, 10 and 15 kg of wet cell mass equivalent/m$^2$. The average transmission is between 30% and 40%.

The results from cleaning the Hydrosart® type#3 module, i.e. the water values prior to and after product run for retentate flow and permeate flux, are depicted in FIG. 7b. The water values both for the retentate flow and for the permeate flux are substantially constant, although the biomass load of the membrane was increased by 500%. This indicates that the blocking problem at the retentate inlet and the blocking problem of the membrane pores have been significantly reduced by the structural changes to the module.

The efficiency of the individual cleaning step is between 93% (worst step efficiency) and 100% (best step efficiency).

Another experiment determined the exact limit of the possible biomass load of the Hydrosart® type#3 module. For this purpose, starting from 15 kg of wet cell mass equivalent/m² biomass load used for initiating the diafiltration, the concentration of inclusion bodies in the retentate was increased at particular times. The results of this experiment are summarized in FIG. 8 (A). For a 50% increase in the biomass concentration in the retentate from 1 153 g of wet cell mass equivalent/l to 1 733 g/l, the retentate flow decreases from 108 l/h to 72 l/h, that is by 33%. For a 70% increase in the biomass load of the membrane from 15 kg of wet cell mass equivalent/m² to 26 kg/m² the permeate flux drops from approx. 16 l/h m² to approx. 7 l/h m², that is by 56%. The upper limit for the biomass load of the membrane thus is about 22 kg of wet cell mass equivalent/m². Above this limit, firstly the permeate flux drops below 10 l/h m² and secondly the retentate flow is clearly reduced further.

A further increase in the possible biomass load to 30 kg of wet cell mass equivalent/m² corresponding to 2 307 g of wet cell mass equivalent/l was not possible in the following cycle and led to blocking of the retentate inlet during the rinsing-in procedure. However, the module was still completely cleanable and, after carrying out the standard cleaning protocol (see Example 2), showed a retentate water value of 122 l/h and a permeate water value of 1 320 l/h m².

In a comparative experiment with the standard Hydrosart® module (0.1 m², Slice format, Lot No. 96108741/No. 008), using portion #3 of the crude homogenate and starting from a biomass load of 3 kg of wet cell mass equivalent/m² (230 g of wet cell mass equivalent/l), the biomass concentration in the retentate was increased stepwise to 10 kg of wet cell mass equivalent/m² (FIG. 8 (B)). The retentate flow and also the permeate flux in the product run are significantly reduced even within one biomass concentration step. At 10 kg of wet cell mass equivalent/m²(769 g of wet cell mass equivalent/l), the permeate fluxes are already only 12–13 l/h m², although only a few permeate volumes have been diafiltered.

Conclusion

The modified Hydrosart® cassette type#3 shows significantly improved performance data, and it was possible to use it over five product runs, the biomass load being increased by 500%. Under the same experimental conditions, the standard Hydrosart® cassette was already irreversibly blocked after three product runs at a biomass load of 3 kg of wet cell mass equivalent/m².

For the channel geometry and screen structure used in type#3, the problem of blockage of the retentate channel over the cycles is no longer evident. Due to the constant conditions within one product cycle and over a plurality of cycles, it is possible to maintain a stable operating point with the Hydrosart® type#3 module even at a biomass load of up to 22 kg of wet cell mass equivalent/m² (1 466 g of wet cell mass equivalent/l).

In direct comparison, the standard Hydrosart® module shows distinctly lower performance data at a significantly lower biomass load.

4.3.2 Effects of Different Crude Homogenate Portions

In an immediately following series of experiments, the Hydrosart® type#3 module was used with a different crude homogenate portion (#3) at a biomass load of 15 kg of wet cell mass equivalent/m², in order likewise to record effects which are generated by a different batch of crude homogenate.

For the new crude homogenate portion #3, the retentate flow in the product run was constant at just 35 l/h over 3 cycles. The permeate flux was constant between 10–15 l/h m² over 3 cycles. The removal was between 40% and 50% and the average transmission between 20% and 30%.

After carrying out the standard cleaning protocol, the water values were constant at 1 300 l/h m² permeate water value and at 100 l/h retentate water value.

Conclusion

Switching to a different batch of crude homogenate (#3) also produces a permeate flux which is comparable to that produced in the previous experiments using the first batch of crude homogenate (#1). The retentate flux was distinctly lower, as in the previous experiments. The cleanability of the Hydrosart® type#3 module remained at a constantly high level.

4.3.3 Operating Point Determination of the Hydrosart® Type#3 Module

FIGS. 9a /9b illustrates an operating point determination of the Hydrosart® type#3 module at a biomass load of 3 kg of wet cell mass equivalent/m² (corresponding to230 g/l). The graphical representation in FIG. 9a corresponds to that chosen by Forman et al. who described an operating point determination for a Durapore® membrane (0.45 µm) at a biomass concentration of 25 g of wet cell mass equivalent/l to 100 g of wet cell mass equivalent/l. When comparing these literature data with the data depicted in FIG. 9a for the modified Hydrosart® type#3 module, the following aspects are noticeable:

The optimal TMP for the modified Hydrosart® type#3 module is 0.35 bar. An increase beyond this optimum leads to a decrease of the permeate flux, and this can be explained by a thickening of the covering layer on the membrane.

The permeate flux produced in this experiment using the Hydrosart® type#3 module is about 20 l/h m². The maximum permeate fluxes produced by the Durapore® module at a biomass concentration of 100 g of wet cell mass equivalent are <8 l/h m². The optimal TMP for the Durapore® membrane is about 0.1 bar.

FIG. 9b illustrates the same operating point determination in a three dimensional representation. A global optimum is present at a TMP of 0.35 bar and a feed of 100 l/h. Additionally, local optima are found at a feed of 70 and 150 l/h and at a TMP of again 0.35 bar.The optimal operating points are summarized once more in an overview in Table 2.

TABLE 2

Global and local operating point optima for the Hydrosart® type#3 module. The global optimum is indicated in bold. The two other operating points represent local optima at which satisfactory permeate fluxes may also be obtained. Biomass load: 3 kg of wet cell mass equivalent/m². Biomass concentration: 230 g of wet cell mass equivalent/l of retentate.

| TMP [bar] | Feed [l/h] | $P_{in}$ [bar] | $P_{out}$ [bar] | $P_{perm}$ [bar] |
| --- | --- | --- | --- | --- |
| 0.35 | 70 | 0.6 | 0.3 | 0.1 |
| 0.35 | 100 | 1.0 | 0.3 | 0.3 |
| 0.35 | 150 | 1.4 | 0.3 | 0.5 |

A transmembrane pressure of 0.35 bar was already earlier found to be optimal, also for the standard Hydrosart® modules (data not shown).

4.3.4 Endotoxin Removal by Crossflow Microfiltration

In independent experiments, at biomass loads of 15 or 45 kg of wet cell mass equivalent/m² of filter area and using the Hydrosart® type#3 module (filter area 0.1 m²), the following results and endotoxin removals were obtained:

| Biomass load kg/m² | Sample | Volume [mL] | Endotoxins [EE/mL] | Total endotoxins [EE]$_{total}$ × 10⁶ | Removal factor |
|---|---|---|---|---|---|
| 15 | Retentate before filtration | 1300 | 240000 | 312 | 1 |
|  | Retentate after filtration | 1300 | 120 00 | 156 | 0.5 |
|  | Permeate$_{total}$ | 5000 | 24000 | 120 |  |
| 45 | Retentate before filtration | 3900 | 240000 | 936 | 1 |
|  | Retentate after filtration | 3900 | 120000 | 468 | 0.5 |
|  | Permeate$_{total}$ | 15000 | 24000 | 360 |  |

The recovery of all endotoxins is approx. 90%. The removal of endotoxins from the retentate into the permeate is about 50%, corresponding to 0.3 log units.

4.3.5 Scale-Up to a 0.6 m² Module Format

Table 3 shows the results of scale-up experiments. These experiments used Hydrosart® modules of type#3 with 0.6 m² of filter area per module (Sartocon ⅔ format). The unit used had in principle the same structure as that described in Example 2. However, the Slice casette holder was exchanged for a Sartocon 3 cassette holder, and the pump was exchanged for an appropriately larger (4 m³/h) rotary piston pump with double face seal (Johnson). The retentate reservoir volume was increased to 5 l and the dead volume of the unit was 2.5 L. The other volumes (e.g. cleaning solutions and wash buffer volumes) were adjusted accordingly

TABLE 3

Summary of the results of experiments on the scale-up of *E. coli* crude homogenate microfiltration. Interleukin-4 R121D Y124D inclusion bodies were used by way of example.

| Parameter | Hydrosart ® type#3 module (0.1 m², Slice) | Hydrosart ® type#3 module (0.6 m², Sartocon 3) |
|---|---|---|
| Scaling factor | 1 | 6 |
| Average retentate flow [l/h] in the product run | 35 ± 5 | 210 ± 20 |
| Average permeate flux [l/h m²] in the product run | 15 ± 5 | 20 ± 10 |
| Removal [%] | 60 ± 20 | 50 ± 5 |
| Transmission [%] | 30 ± 5 | 40 ± 5 |
| Retentate water value [l/h] | 100 ± 10 | 600 ± 50 |
| Permeate water value [l/h] | 1 300 ± 200 | 1 300 ± 200 |

The data represent averages from, in each case, 3 independent experiments which were carried out under the same standardized conditions (filtration and cleaning conditions, see Example 2).

Conclusion

The data compiled in Table 3 illustrate that linear scaling is possible for the Hydrosart® type#3 module, with the performance data of the Sartocon 3-module format changing in accordance with those of the Slice module format. Scale-up by a factor of 6 results in the retentate flow in the product run being raised by exactly a factor of 6. Correspondingly, the retentate water value is increased by a factor of 6. The other performance data such as permeate flux in the product run, permeate water value, removal and transmission remain the same within the accuracy limits of the particular determination.

References Cited

Apeler H, Wehlmann H (1998): Plasmids, their construction and their use in the manufacture of Interleukin-4 and Interleukin-4 muteins. European Patent application EP 00100129.6, filed Jan. 7, 2000.

Bailey S M & Meagher M M (1997): J. Membr. Sci. 131: 29–38

Bailey S M and Meagher M M (1997): Biotechnol. Bioeng. 56(3): 304–310

Blum P et al. (1992): Bio/Technology 10: 301–304

Bowden G A, Paredes A M, Georgiou G (1991): Bio/Technology 9: 725–730

Forman S M, DeBernardez E R, Feldberg R S, Swartz R W (1990): J. Membr. Sci. 48: 263–279

Marston FAO (1986): Biochem. J. 240: 1–12

Meagher M M, Barlett R T, Rai V R, Khan F R (1994): Biotechnol. Bioeng. 43: 969–977

Meyeroltmanns F (1991): BioTec 5: 918–921

Riesenberg D, Menzel K, Schulz V, Schumann K, Veith G, Zuber G, Knorre W A (1990): Appl. Microbiol. Biotechnol. 34: 77–82

Schoemaker J M, Brasnett A H, Marston FAO (1985): EMBO J 4: 775–780

Schoner R G, Ellis F L, Schoner B E (1985): Biotechnology 3:151–154

Sebald W (1998): Therapeutic agents which are antagonists or partial agonists of human Interleukin-4, U.S. Pat. No. 5,723,118, May 3, 1998. Human IL-4 mutant proteins, Eur. Patent 0 613 499 B1, Nov. 2, 1998.

Sharma S K (1986): J. Biotechnol. 4: 119–124

Taylor G, (1986): Bio/Technology 4: 553–557

Figure 1:
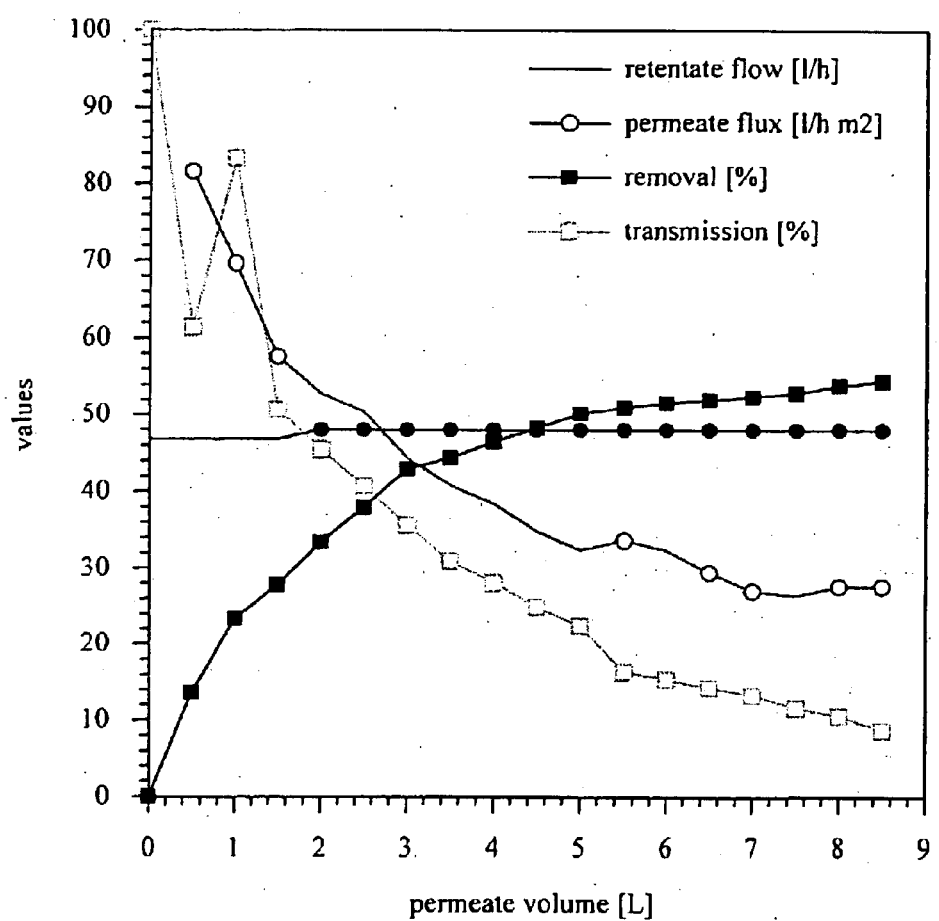
FIG. 1 Diafiltration of *E. coli* crude homogenate (portion #1) with inclusion bodies of interleukin-4 R121D Y124D. 1st product cycle with a newly purchased Hydrosart® Slice standard module (0.1 m²) 3051860601 W—SG, Lot no. 96108741/13. 300 g of wet cell mass equivalent (3 kg of wet cell mass equivalent/m²). Total retentate volume 2.55 l (117 g of wet cell mass equivalent/l).
Figure 2:
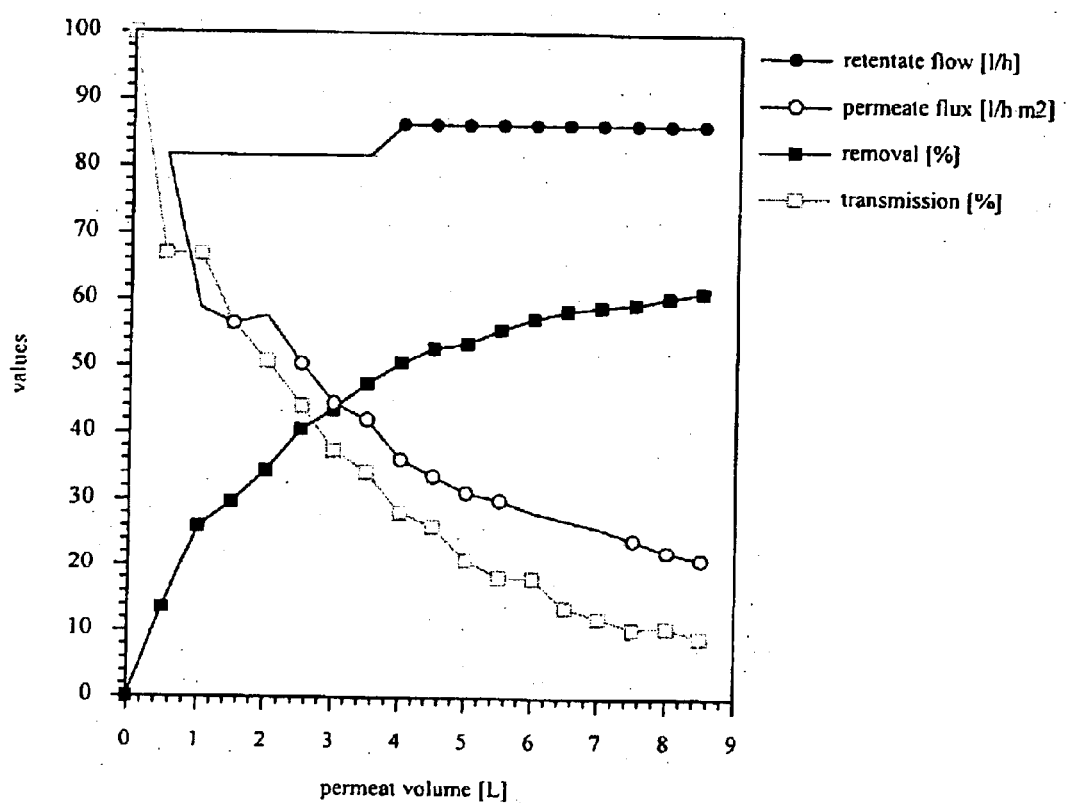
FIG. 2 Diafiltration of *E. coli* crude homogenate (portion #1) with inclusion bodies of interleukin-4 R121D Y124D. 1st product cycle with a newly purchased modified Hydrosart® Slice module type#1 (0.1 m²), Lot no. 98025101. 300 g of wet cell mass equivalent (3 kg of wet cell mass equivalent/m²). Total retentate volume 2.55 l (117 g of wet cell mass equivalent/l).
Figure 3A:
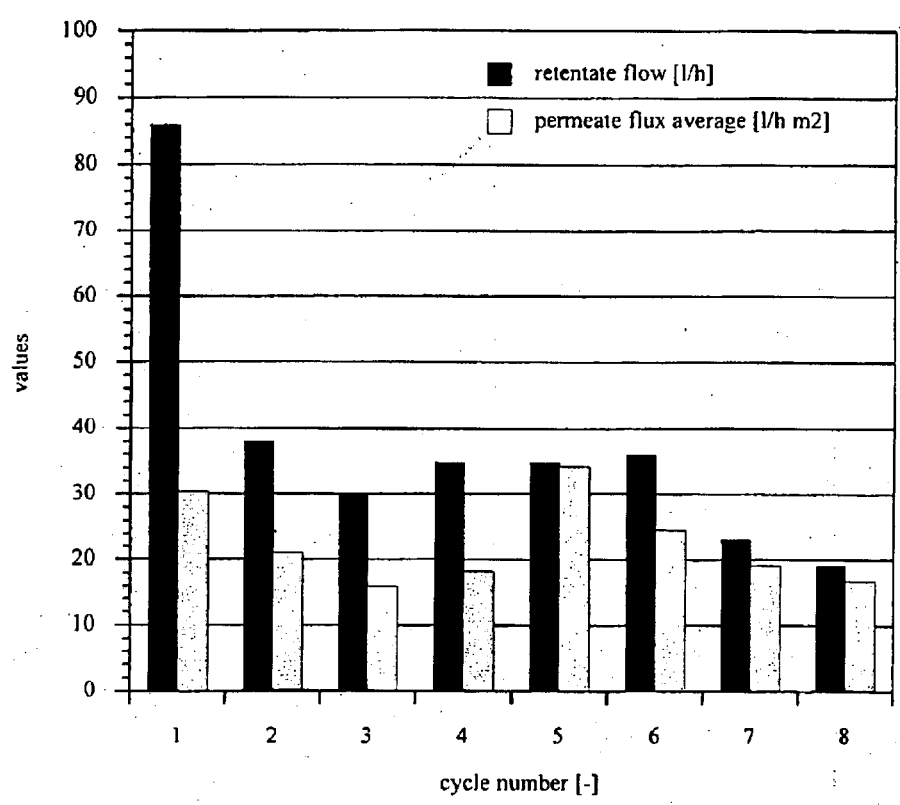
FIG. 3*a* Retentate flow (l/h) and average permeate flux (l/h m²) in the product run as functions of the cycle number. Diafiltration of *E. coil* crude homogenate (portion #1) with inclusion bodies of interleukin-4 R121D Y124D. 1st to 9th product cycles with a newly purchased modified Hydrosart® Slice module type#1 (0.1 m²), Lot no. 98025101. 300 g of wet cell mass equivalent (3 kg of wet cell mass equivalent/m²). Total retentate volume 2.55 l (117 g of wet cell mass equivalent/l).
Figure 3B:
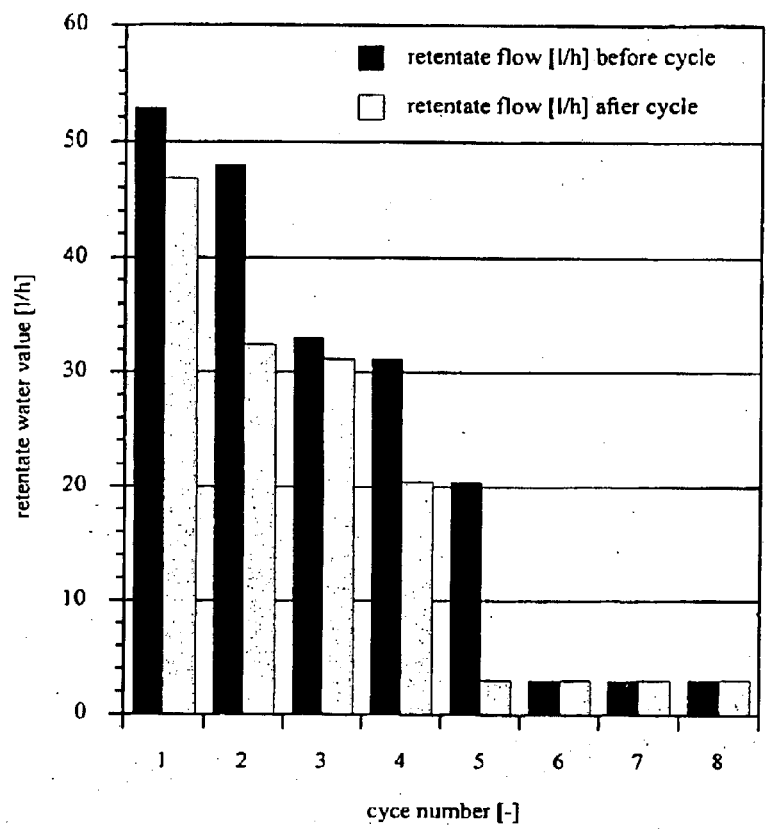
FIG. 3*b* Water values before and after product run. Retentate flow (l/h) and permeate flux (l/h m²) as functions of the cycle number. Diafiltration of *E. coli* crude homogenate (portion #1) with inclusion bodies of interleukin-4 R121D Y124D. 1st to 9th product cycles with a newly purchased modified Hydrosart® Slice module type#1 (0.1 m²), Lot no. 98025101. 300 g of wet cell mass equivalent (3 kg of wet cell mass equivalent/$m^2$). Total retentate volume 2.55 l (117 g of wet cell mass equivalent/l).
Figure 3B:
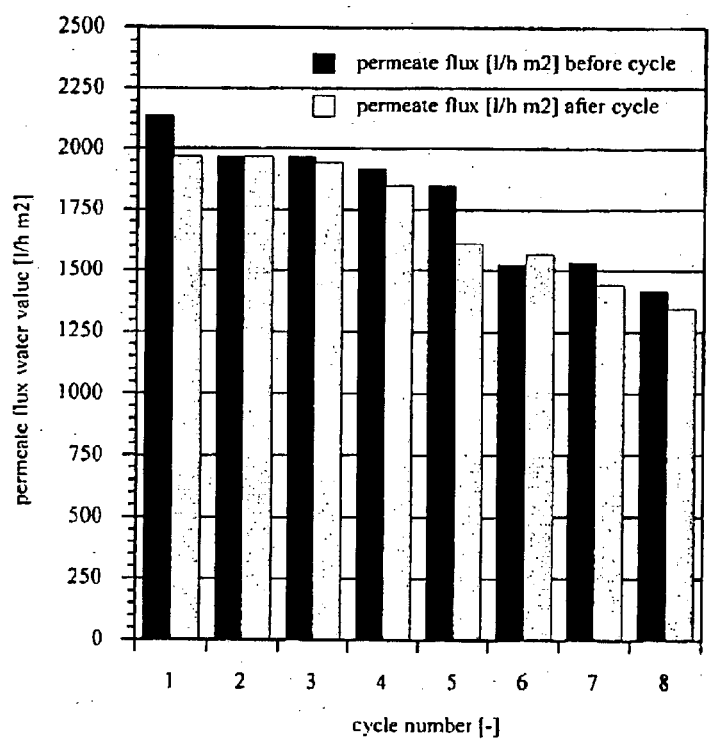
Figure 4:
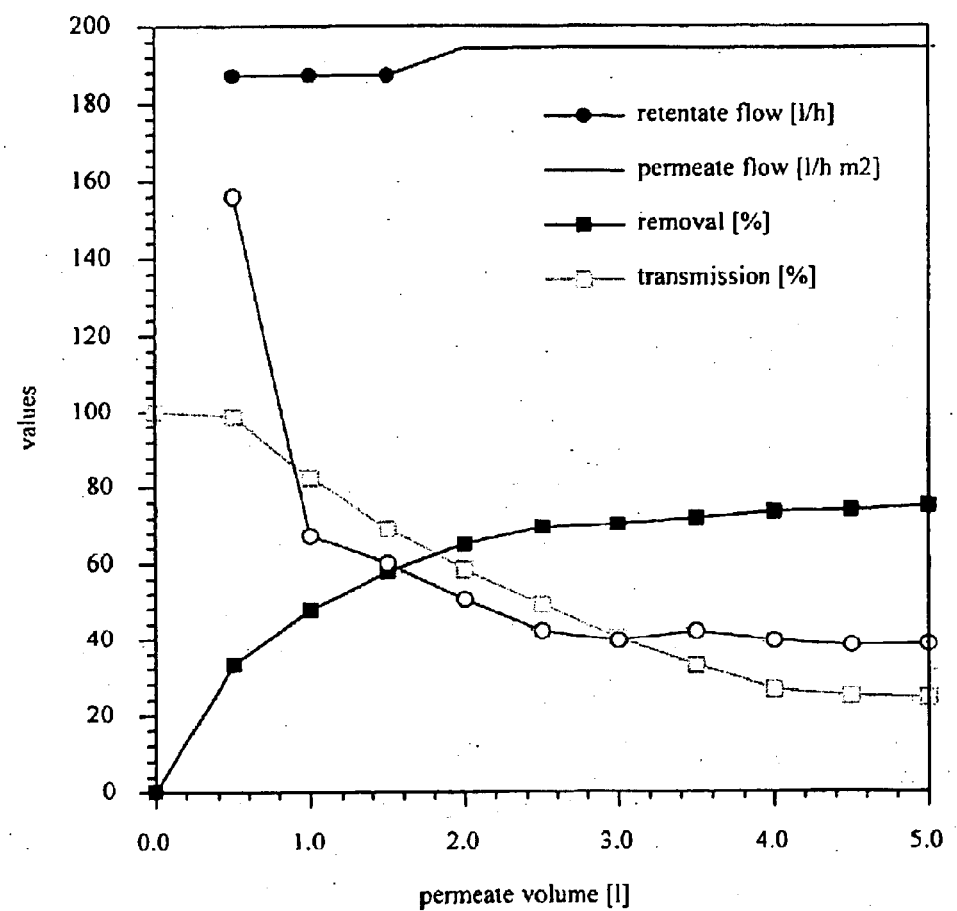
Figure 5A:
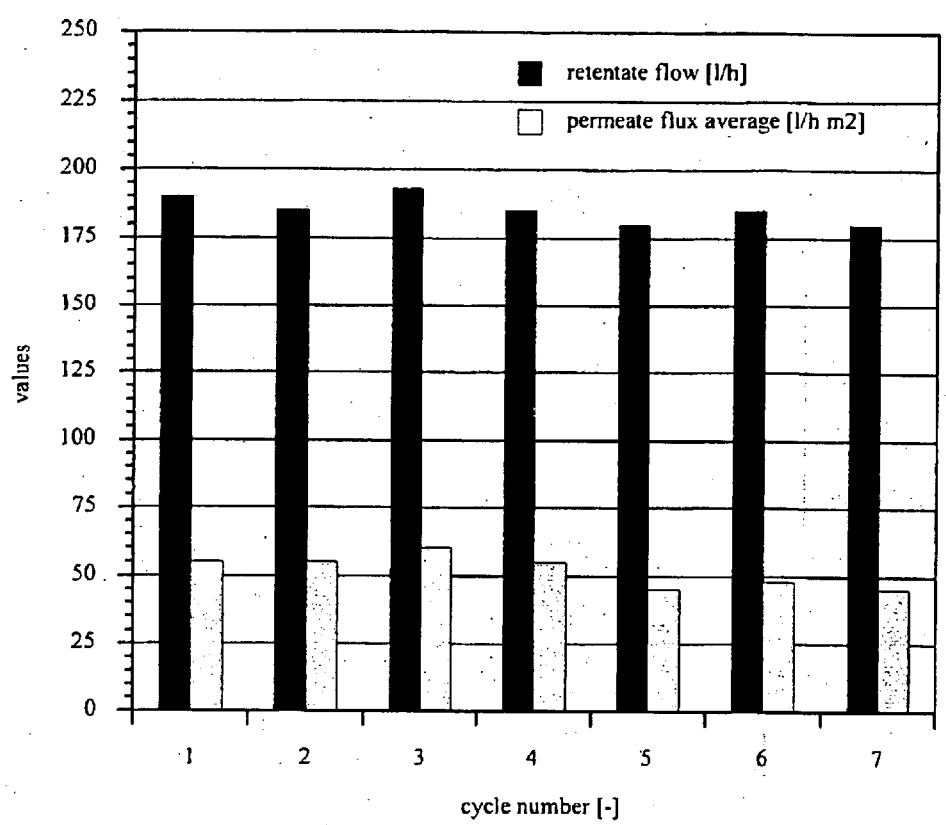
Figure 5B:
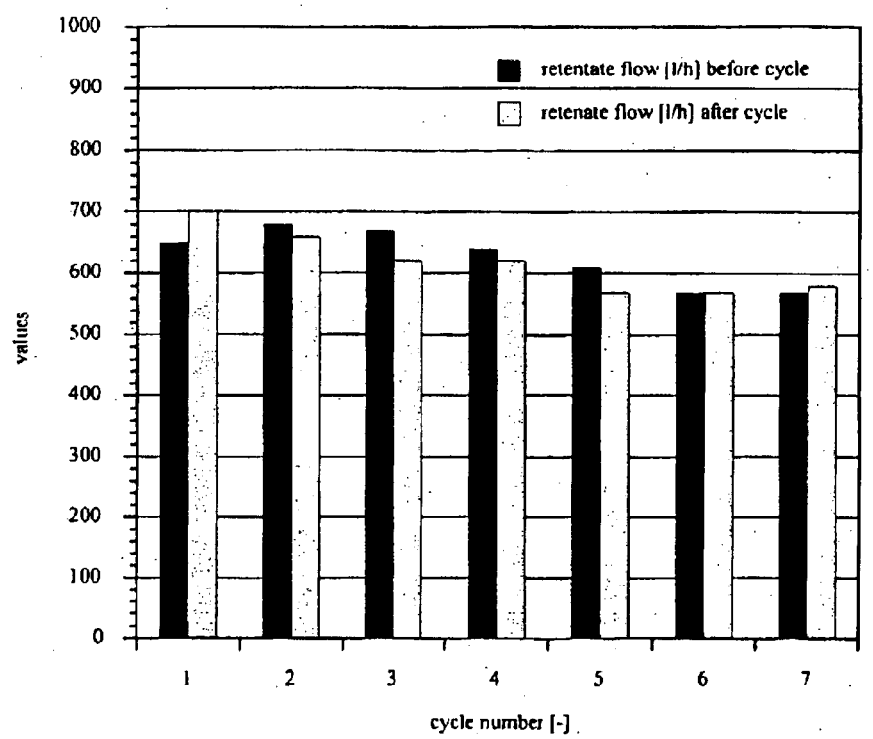
Figure 5B:
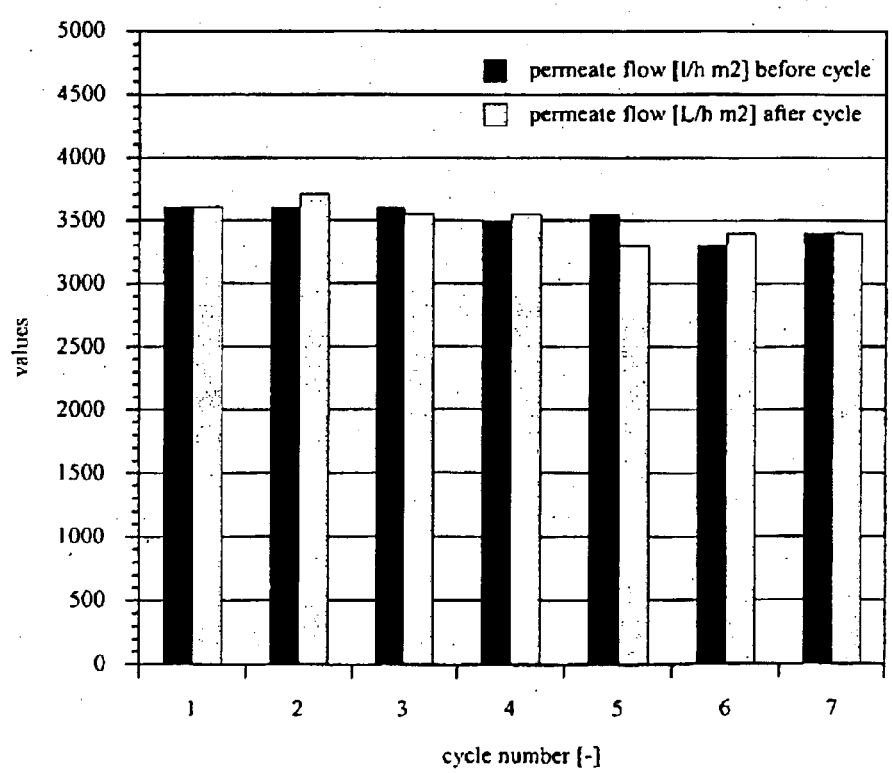
Figure 6:
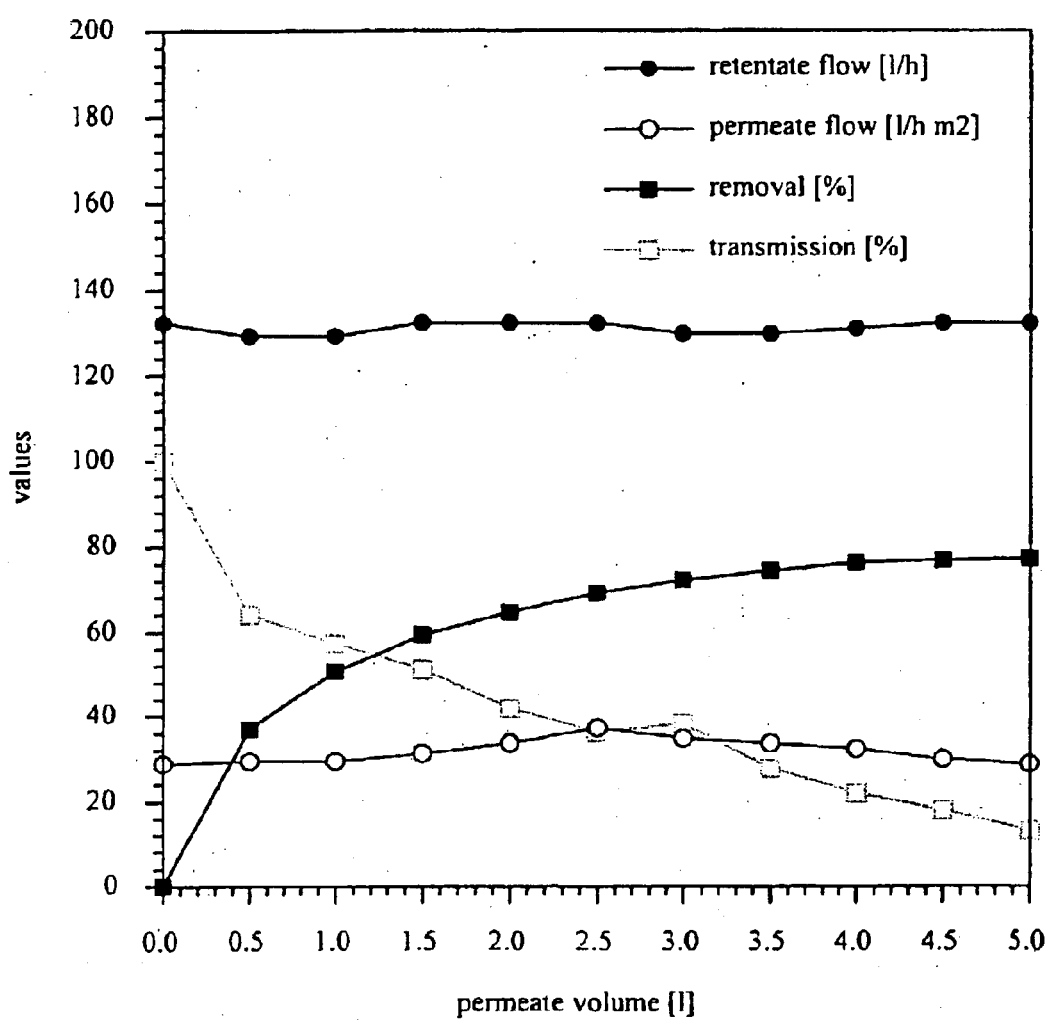
Figure 7A:
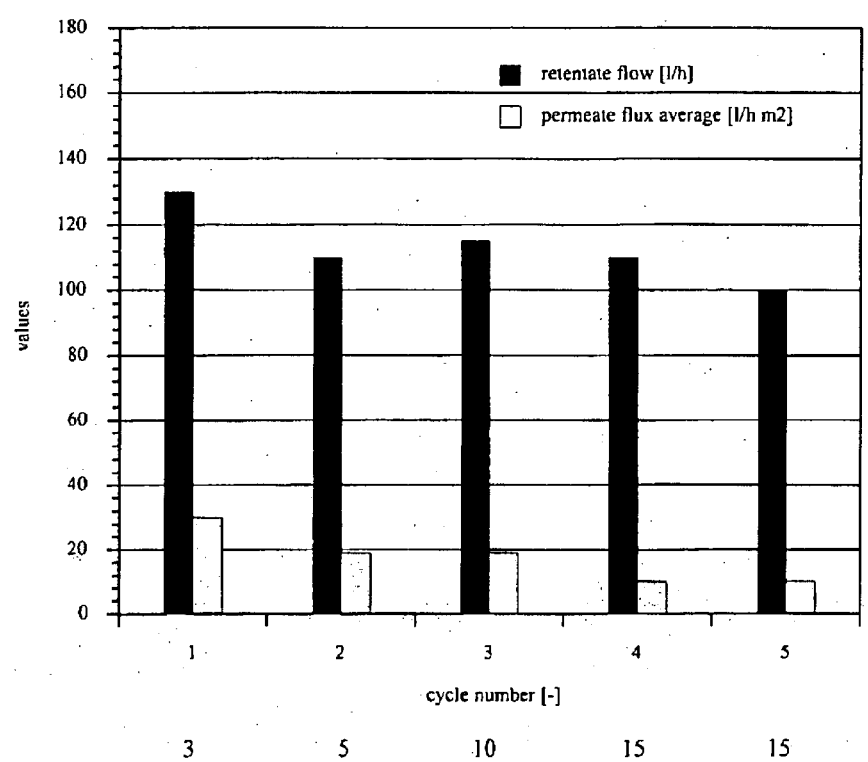
Figure 7B:
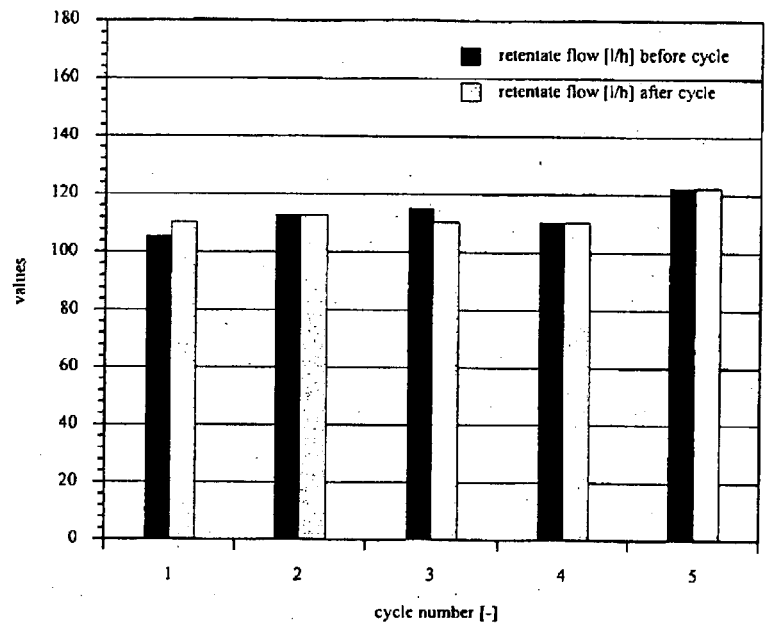
Figure 7B:
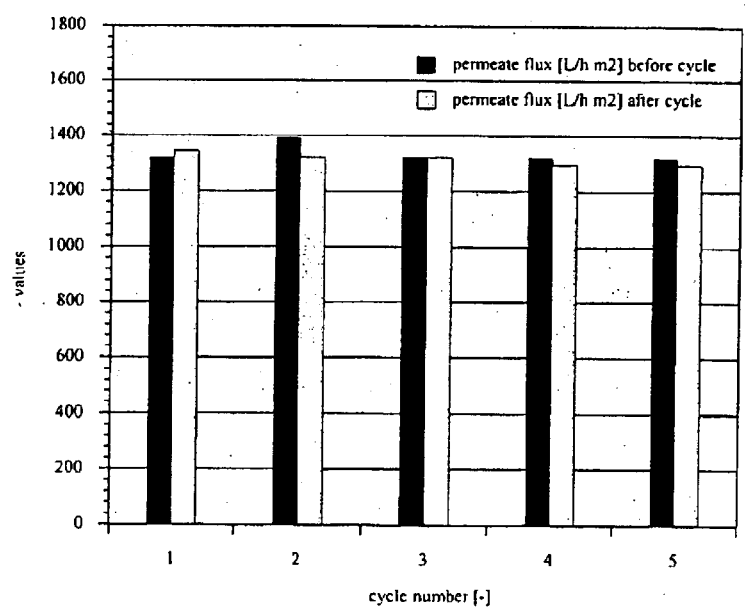
Figure 8:
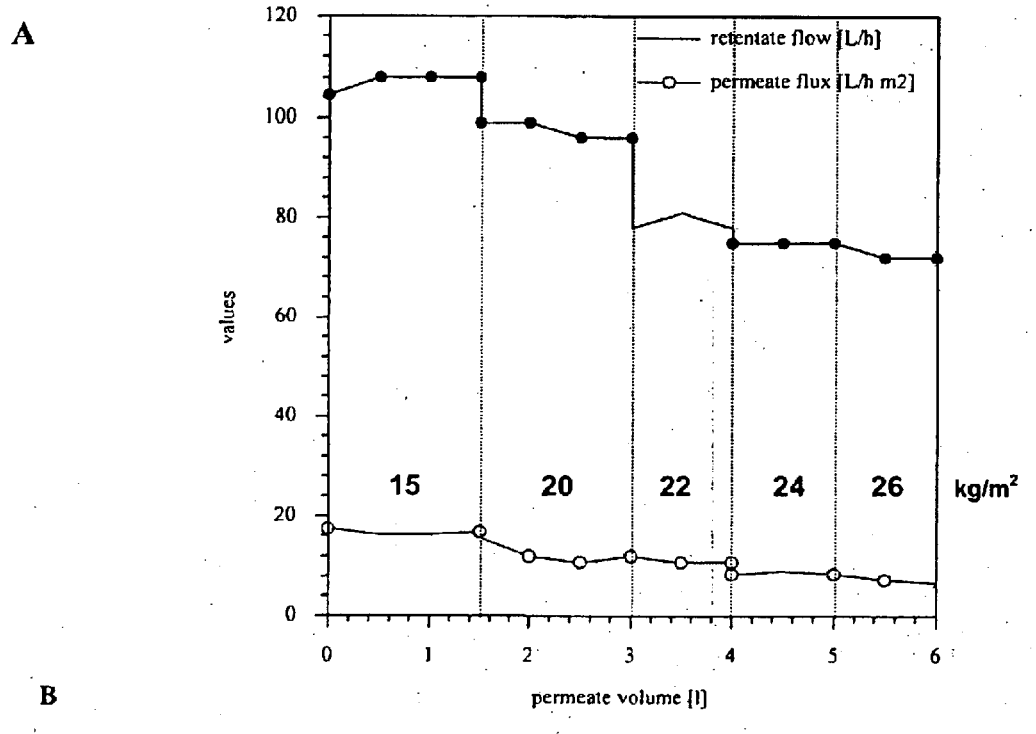
Figure 8:
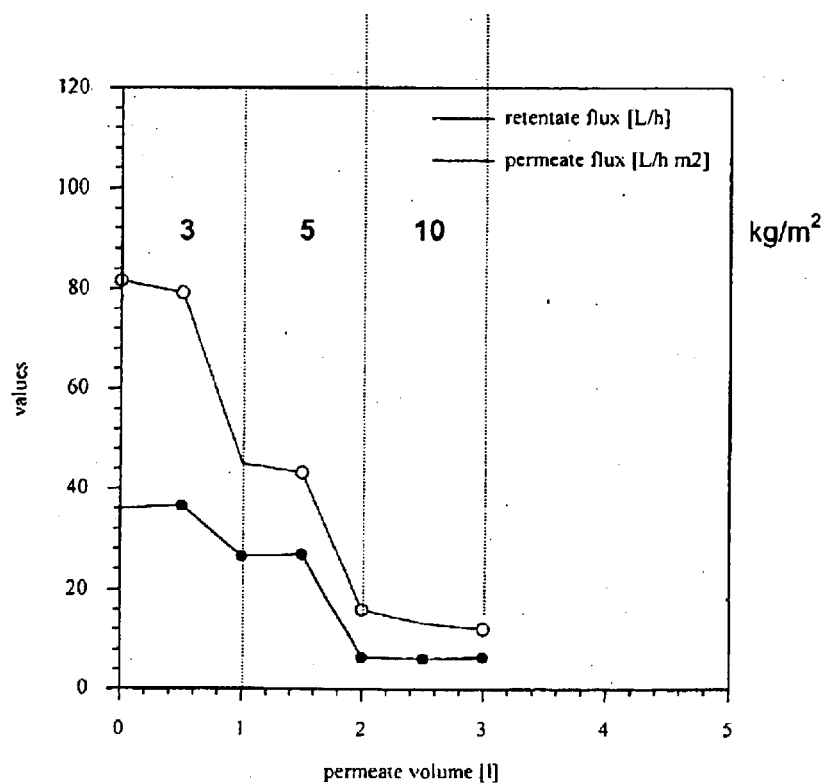
Figure 9A:
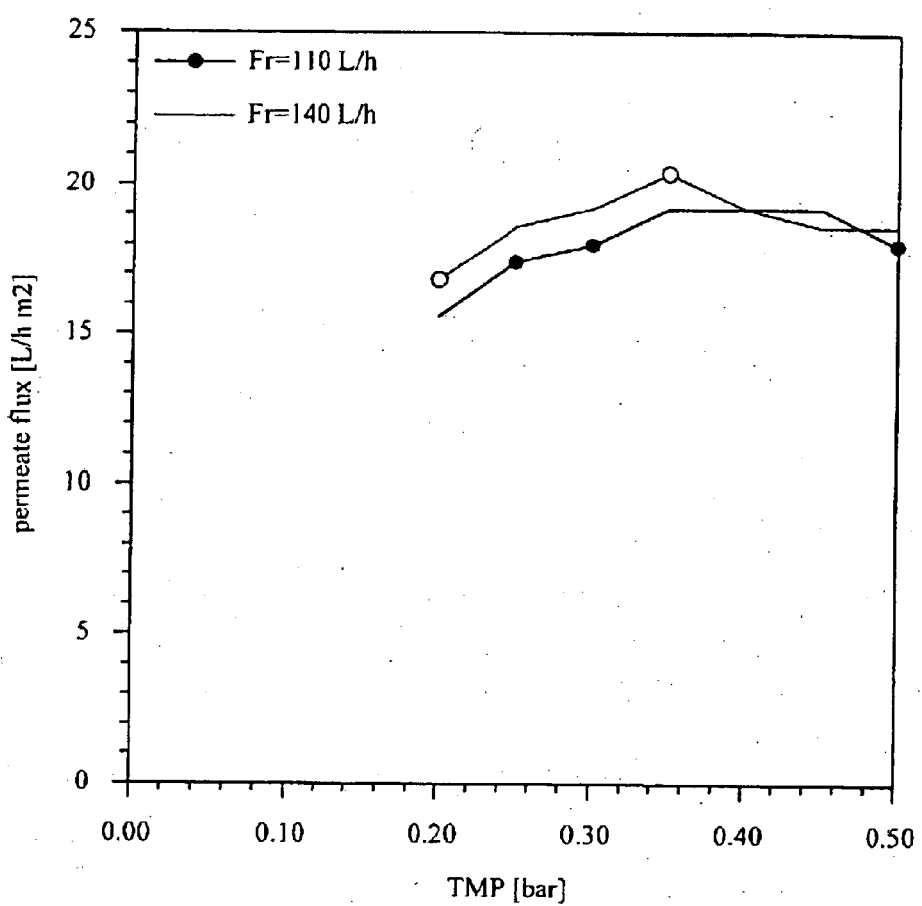
Figure 9B:
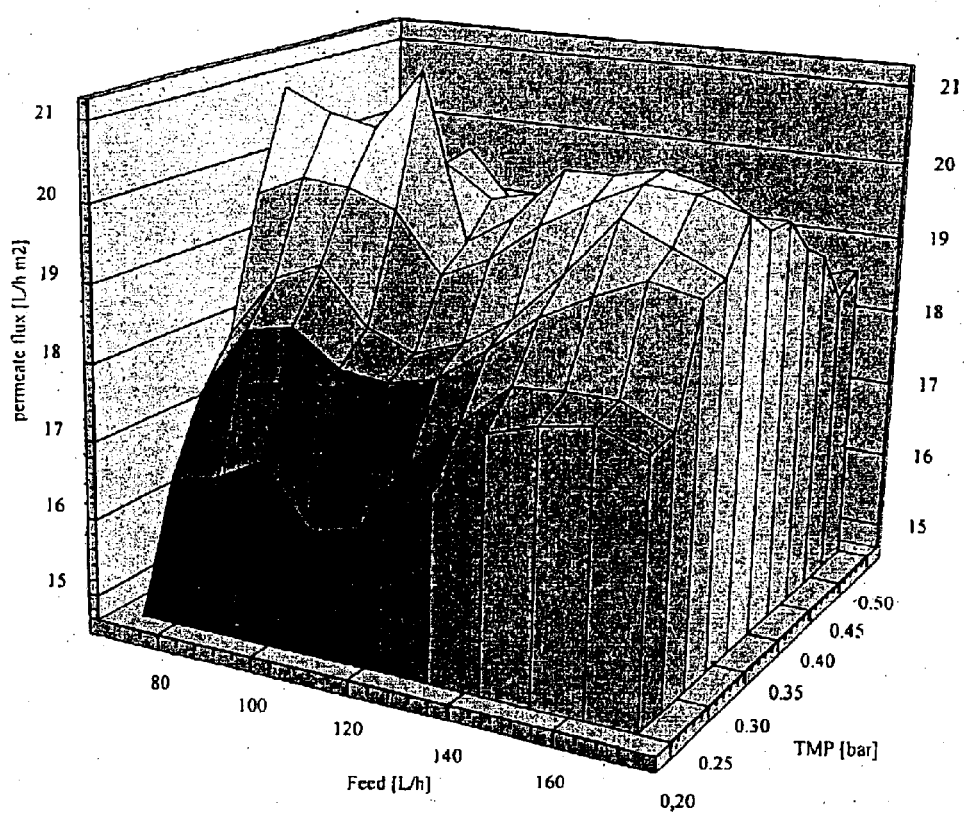
Figure 10:
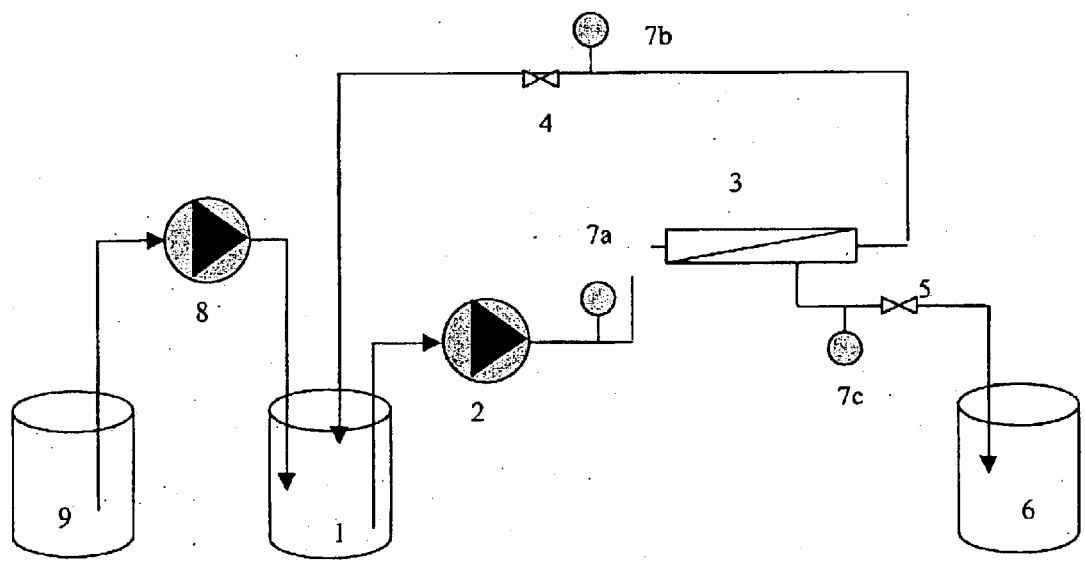

FIG. 4 Diafiltration of *E. coli* crude homogenate (portion #1) with inclusion bodies of interleukin-4 R121D Y124D. 1st product cycle with a newly purchased modified Hydrosart® Slice module type#2 (0.05 $m^2$), Lot no. 98055101. 300 g of wet cell mass equivalent (3 kg of wet cell mass equivalent/$m^2$). Total retentate volume 1.3 l (230 g of wet cell mass equivalent/l).

FIG. 5*a* Retentate flow (l/h) and average permeate flux (l/h $m^2$) at product run as functions of the cycle number. Diafiltration of *E. coli* crude homogenate (portion #1) with inclusion bodies of interleukin-4 R121D Y124D. 1st to 7th product cycles with a newly purchased modified Hydrosart® Slice module type#2 (0.05 $m^2$), Lot no. 98055101. 300 g of wet cell mass equivalent (3 kg of wet cell mass equivalent/$m^2$). Total retentate volume 1.3 l (230 g of wet cell mass equivalent/l).

FIG. 5*b* Water values before and after product run. Retentate flow (l/h) and permeate flux (l/h $m^2$) as functions of the cycle number. Diafiltration of *E. coli* crude homogenate (portion #1) with inclusion bodies of interleukin-4 R121D Y124D. 1st to 7th product cycles with a newly purchased modified Hydrosart® Slice module type#2 (0.05 $m^2$), Lot no. 98055101. 300 g of wet cell mass equivalent (3 kg of wet cell mass equivalent/$m^2$). Retentate volume 1.3 l (230 g of wet cell mass equivalent/l).

FIG. 6 Diafiltration of *E. coli* crude homogenate (portion #2) with inclusion bodies of interleukin-4 R121D Y124D. 1st product cycle with a newly purchased modified Hydrosart® Slice module type#3 (0.1 $m^2$), Lot no. 99015111. 300 g of wet cell mass equivalent (3 kg of wet cell mass equivalent/$m^2$). Retentate volume 1.3 l (230 g of wet cell mass equivalent/l).

FIG. 7*a* Retentate flow (l/h) and average permeate flux (l/h $m^2$) at product run as functions of the cycle number for an increase in the biomass load of the membrane. Diafiltration of *E. coli* crude homogenate (portion #2) with inclusion bodies of interleukin-4 R121D Y124D. 1st to 5th product cycles with a newly purchased modified Hydrosart#Slice module type#3 (0.1 $m^2$), Lot no. 99015111. 3 kg of wet cell mass equivalent/$m^2$, 5 kg/$m^2$, 10 kg/$m^2$, 15 kg/$m^2$, corresponding to 230 g of wet cell mass equivalent/l, 384 g/l, 770 g/l, 1 153 g/l.

FIG. 7*b* Water values before and after product run. Retentate flow (l/h) and permeate flux (l/h $m^2$) as functions of the cycle number. Diafiltration of *E. coli* crude homogenate (portion #2) with inclusion bodies of interleukin-4 R121D Y124D. 1st to 5th product cycles with a newly purchased modified Hydrosart® Slice module type#3 (0.1 $m^2$), Lot no. 99015111. 3 kg of wet cell mass equivalent/$m^2$, 5 kg/$m^2$, 10 kg/$m^2$, 15 kg/$m^2$, corresponding to 230 g of wet cell mass equivalent/l, 384 g/l, 770 g/l, 1 1153 g/l.

FIG. 8 Stepwise increase in the biomass load

A. Diafiltration of *E. coli* crude homogenate (portion #2) with inclusion bodies of interleukin-4 R121D Y124D with a modified Hydrosart® Slice module type#3 (0.1 $m^2$), Lot no. 99015111. Starting conditions: 1 500 g of wet cell mass equivalent (15 kg of wet cell mass equivalent/$m^2$). Retentate volume 1.3 l (1 153 g of wet cell mass equivalent/l). Stepwise increase in the biomass load of the membrane to 20, 22, 24 and finally 26 kg of wet cell mass equivalent/$m^2$ at the times indicated in the graph during the continuing diafiltration. Due to the volume change in the retentate, this correspondingly results in 1 176 g of wet cell mass equivalent/l, 1 466 g/l, 1 600 g/l and finally 1 733 g/l).

B. Diafiltration of *E. coli* crude homogenate (portion #3) with inclusion bodies of interleukin-4 R121D Y124D with a standard Hydrosart® Slice module (0.1 $m^2$), Lot no. 96 108741/008. Starting conditions: 300 g of wet cell mass equivalent (3 kg of wet cell mass equivalent/$m^2$). Retentate volume 1.3 l (230 g of wet cell mass equivalent/l). Stepwise increase in the biomass load of the membrane to 5 kg and finally 10 kg of wet cell mass equivalent/$m^2$ at the times indicated in the graph during the continuing diafiltration. The experiment was then aborted owing to the low permeate fluxes. The retentate volume was held constant at 1.3 L. This results correspondingly in biomass concentrations in the retentate of 384 g of wet cell mass equivalent/l and 769 g/l.

FIG. 9*a* Operation point determination of the modified Hydrosart® type#3 module. Biomass load 3 kg of wet cell mass equivalent/$m^2$ (230 g of wet cell mass equivalent/l), crude homogenate portion #2. The permeate flux is plotted as a function of the transmembrane pressure (TMP). The retentate flow ($F_r$) was fixed at approx. 110 l/h or approx. 140 l/h. The experiment was carried out with complete recycling of all volume flows.

FIG. 9*b* Operation point determination of the modified Hydrosart type#3 module. Biomass load 3 kg of wet cell mass equivalent/$m^2$ (corresponding to 230 g of wet cell mass equivalent/l), crude homogenate portion #2. The permeate flux is plotted as a function of the transmembrane pressure (TMP) and the feed (=retentate flow+permeate flow). The experiment was carried out with complete recycling of all volume flows.

FIG. 10 Schematic representation of the experimental setup of a crossflow microfiltration unit

| # | Description |
|---|---|
| 1 | Retentate resevoir (stirred) with level indicator (Control for wash buffer pump (9)) |
| 2 | Rotary piston pump |
| 3 | Cassette holder (Sartocon Slice format, Sartorius AG, Germany) equipped with Hydrosart ® Slice cassette (0.1 $m^2$ filtration area) |
| 4 | Flow resistrictor valve retentate outlet |
| 5 | Flow restrictor valve permeate outlet |
| 6 | Permeate receiver |
| 7 | Pressure gauge R(in) = 7a; R(out) = 7b; P = 7c |
| 8 | Wash buffer pump |
| 9 | Wash buffer resevoir |

The dead volume of the system used is 0.55 L.

What is claimed is:

1. A process for purifying and/or concentrating a biomass load of inclusion bodies in a solution, which is characterized in that the inclusion body-containing solution is directed tangentially past one or more semipermeable membranes so that the membranes retain the inclusion bodies and that substances or components having a relatively small molecular weight or particle diameter can pass through, thus obtaining a purified and/or concentrated inclusion body solution, and on the semipermeable membrane a planar net matrix is located which is constructed of intersecting longitudinal and transverse filaments such that the adjacent longitudinal and transverse filaments are, in each case, at a distance from one another which is 5 to 15 times greater than their thickness which is in the range from 150 to 600 $\mu$m, said matrix having a membrane to matrix distance of about 80 $\mu$m, a matrix thickness of about 760 $\mu$m, a filament thickness of about 340–450 $\mu$m and a filament distance of about 2400 $\mu$m.

2. The process according to claim 1, characterized in that the biomass load of the membrane is greater than 65 g of wet cell mass equivalent/$m^2$.

3. The process according to claim 1, characterized in that the biomass load of the membrane is greater than 650 g of wet cell mass equivalent/$m^2$.

* * * * *